United States Patent
Seo et al.

(10) Patent No.: US 12,319,907 B2
(45) Date of Patent: Jun. 3, 2025

(54) COMPOSITION OF CULTURE MEDIA FOR FAECALIBACTERIUM PRAUSNITZII

(71) Applicant: ENTEROBIOME INC., Goyang-si (KR)

(72) Inventors: Jae Gu Seo, Gimpo-si (KR); Do Kyung Lee, Seoul (KR)

(73) Assignee: ENTEROBIOME INC. (KR)

( * ) Notice: Subject to any disclaimer, the term of this patent is extended or adjusted under 35 U.S.C. 154(b) by 0 days.

(21) Appl. No.: 17/764,371

(22) PCT Filed: Feb. 7, 2022

(86) PCT No.: PCT/KR2022/001867
§ 371 (c)(1),
(2) Date: Mar. 28, 2022

(87) PCT Pub. No.: WO2023/090536
PCT Pub. Date: May 25, 2023

(65) Prior Publication Data
US 2024/0043789 A1  Feb. 8, 2024

(30) Foreign Application Priority Data
Nov. 18, 2021 (KR) .................. 10-2021-0159492

(51) Int. Cl.
*C12N 1/20* (2006.01)
(52) U.S. Cl.
CPC ..................... *C12N 1/20* (2013.01)
(58) Field of Classification Search
None
See application file for complete search history.

(56) References Cited

U.S. PATENT DOCUMENTS

2018/0094233 A1* 4/2018 Belzer .................. C12N 1/20
2020/0121738 A1* 4/2020 Cutcliffe .............. A61K 35/741

FOREIGN PATENT DOCUMENTS

| KR | 102169794 B1 | 10/2020 |
| KR | 102222953 B1 | 3/2021 |
| KR | 102245415 B1 | 4/2021 |
| WO | 2021016081 A1 | 1/2021 |

OTHER PUBLICATIONS

Millipore Sigma. https://www.sigmaaldrich.com/US/en/technical-documents/technical-article/cell-culture-and-cell-culture-analysis/mammalian-cell-culture/cysteine?srsltid=AfmBOopycgWhpOJY1EQeERt0xPE1VpvnplP3sg9Z7MTPqIOPKDMsSb14 ; 2024.*
Martin et al (Front. Microbiol., Jun. 29, 2017. Sec. Food Microbiology; vol. 8, pp. 1-13).*
Ndongo et al (Human Microbe Journal. Mar. 2020. vol. 15, pp. 1-10).*
Communication regarding the European Search Report issued in EP Patent Application No. 22714102.5, mailed on Sep. 28, 2023.
D'hoe, Kevin, et al. "Integrated culturing, modeling and transcriptomics uncovers complex interactions and emergent behavior in a three-species synthetic gut community." Elife 7 (2018): e37090. DOI: https://doi.org/10.7554/elife.37090.
Communication issued in EP Patent Application No. 22714102.5, mailed on Oct. 10, 2023.
Notice of reasons of refusal in JP Patent Application No. 2022-520672 dated Dec. 21, 2020.
Canadian Office Action in related application No. 3,152,604, dated Apr. 6, 2023, 4 pages.

* cited by examiner

Primary Examiner — Jennifer E Graser
(74) Attorney, Agent, or Firm — Dilworth IP, LLC

(57) ABSTRACT

The present invention relates to a medium composition for culturing *Faecalibacterium prausnitzii* composed of vegetable peptone, yeast extract, a phosphate compound, a carbonate compound, cyanocobalamin (B12), L-cysteine, ammonium acetate, and maltose, and a method of mass-culturing *Faecalibacterium prausnitzii* using the medium composition. When the medium composition and the method for culturing *Faecalibacterium prausnitzii* according to the present invention are used, high-density culture and mass production of strains of *Faecalibacterium prausnitzii* phylogroup II are possible. In addition, when *Faecalibacterium prausnitzii* is mass-cultured in the medium composition free of animal components, it may be cultured at high density even in high-concentration anaerobic nitrogen gas, and thus it is possible to provide a culture method which is more economical and suitable for industrialization.

5 Claims, 14 Drawing Sheets

[FIG 1]
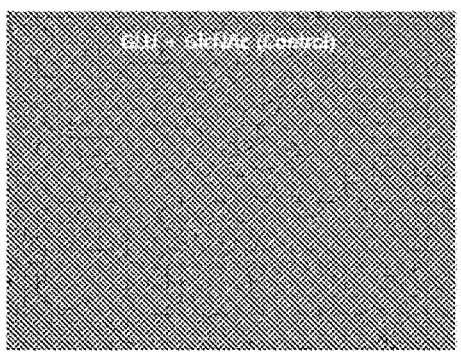
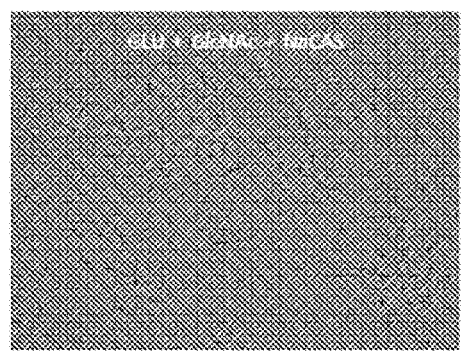
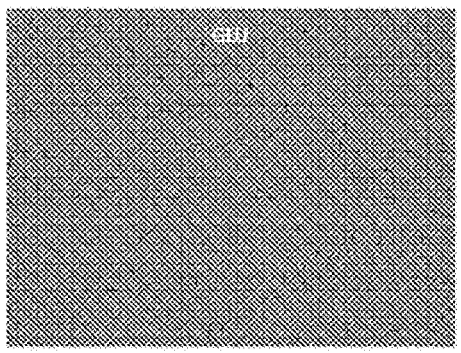
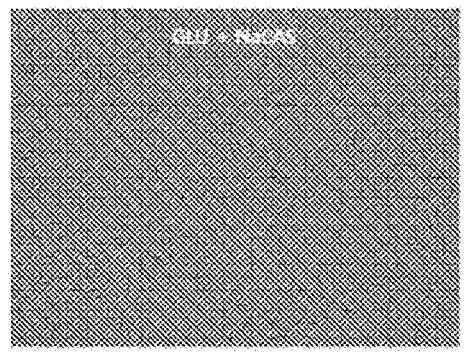

[FIG 2]
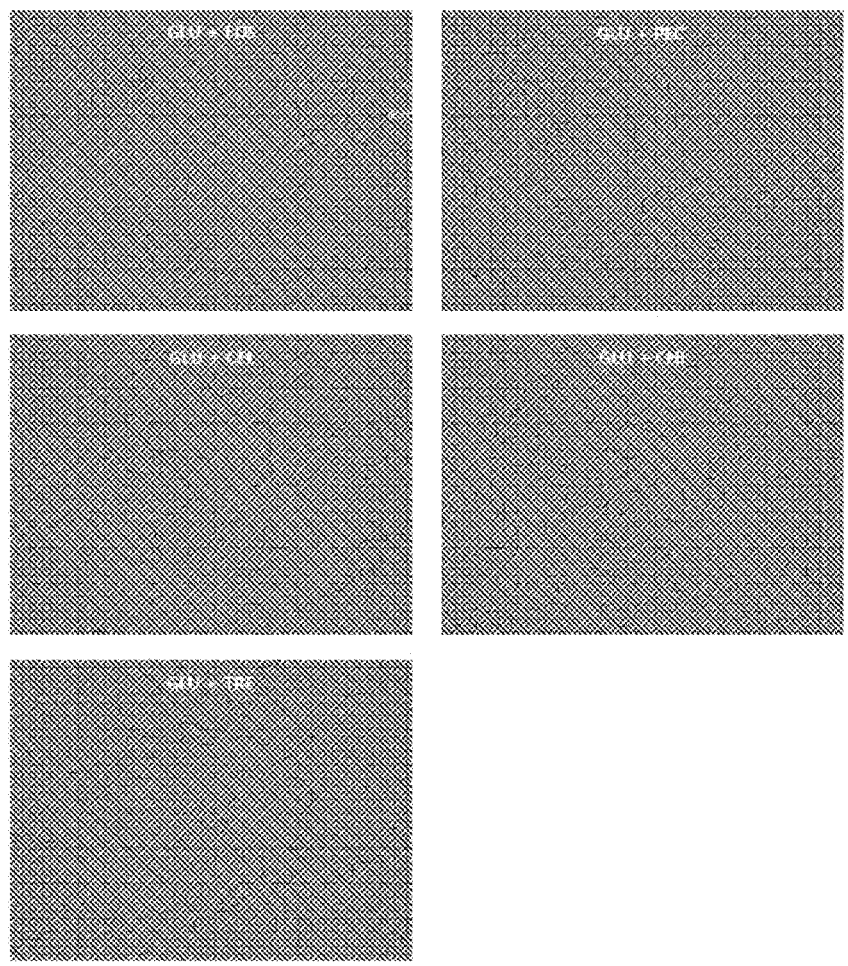

[FIG 3]
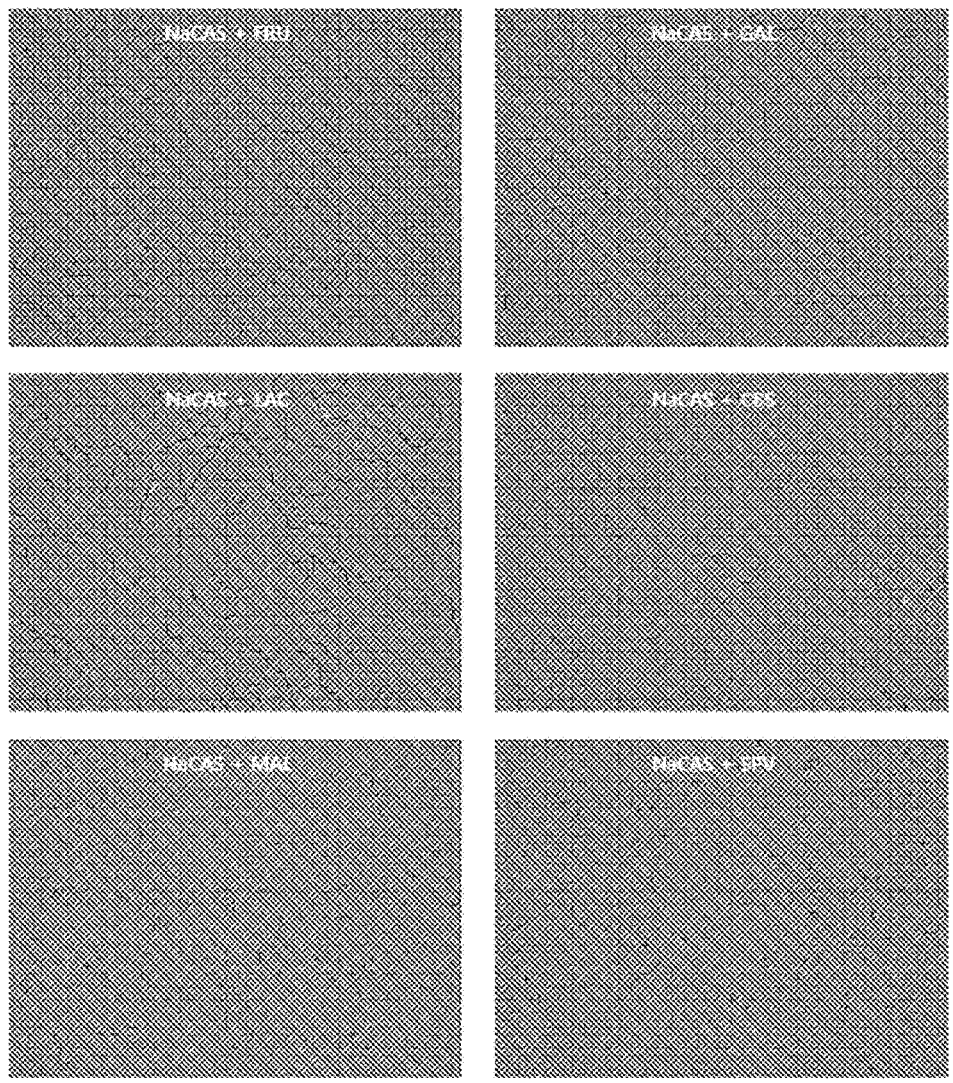

[FIG 4A]
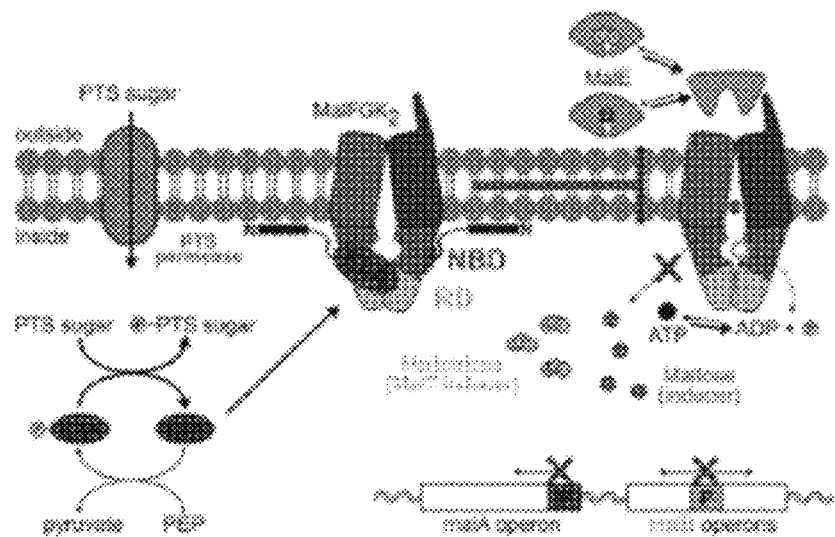
[FIG 4B]
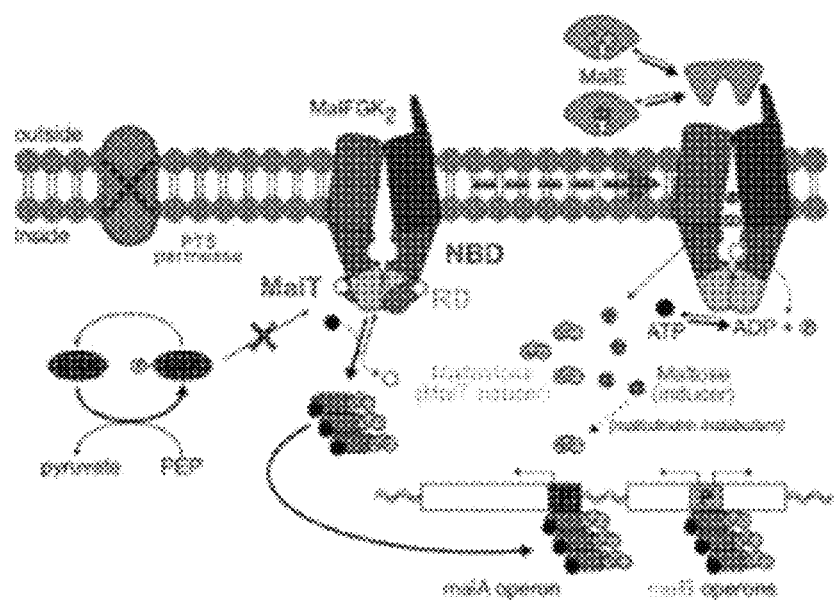

[FIG 5]
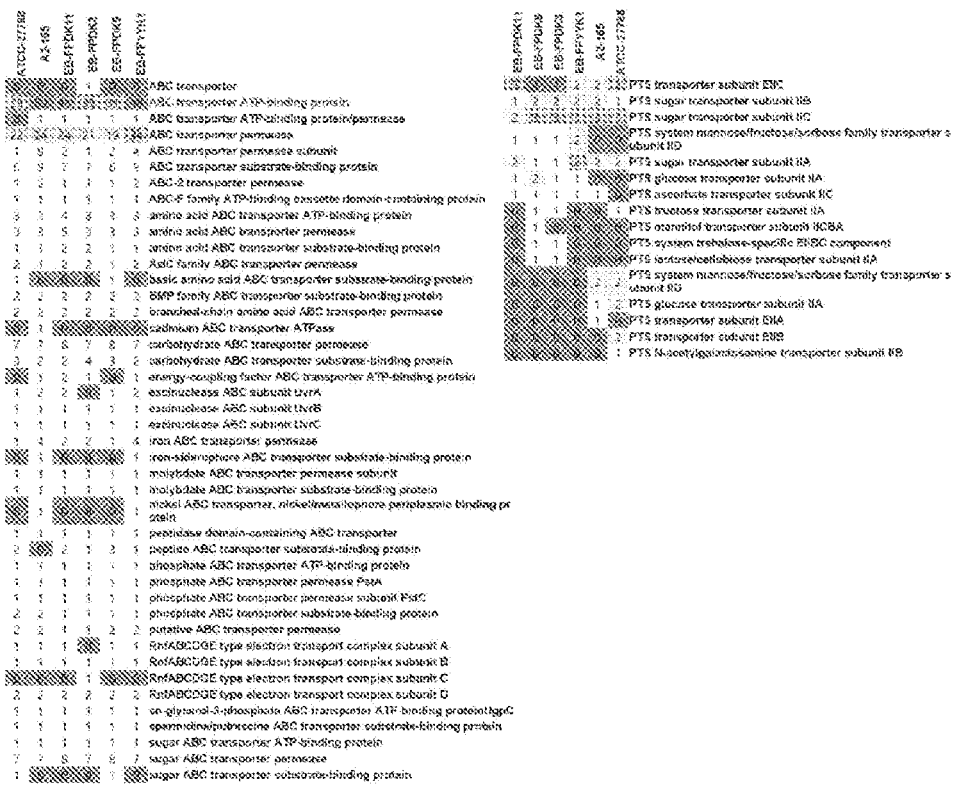

[FIG 6]
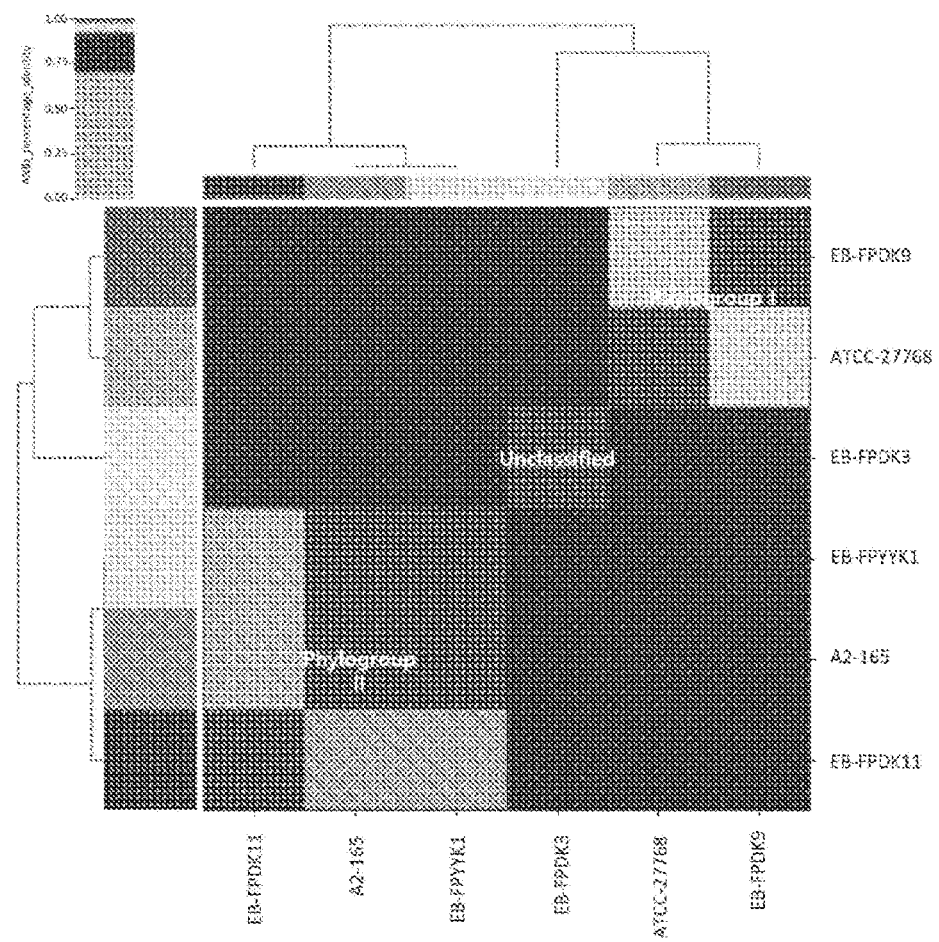

[FIG 7]
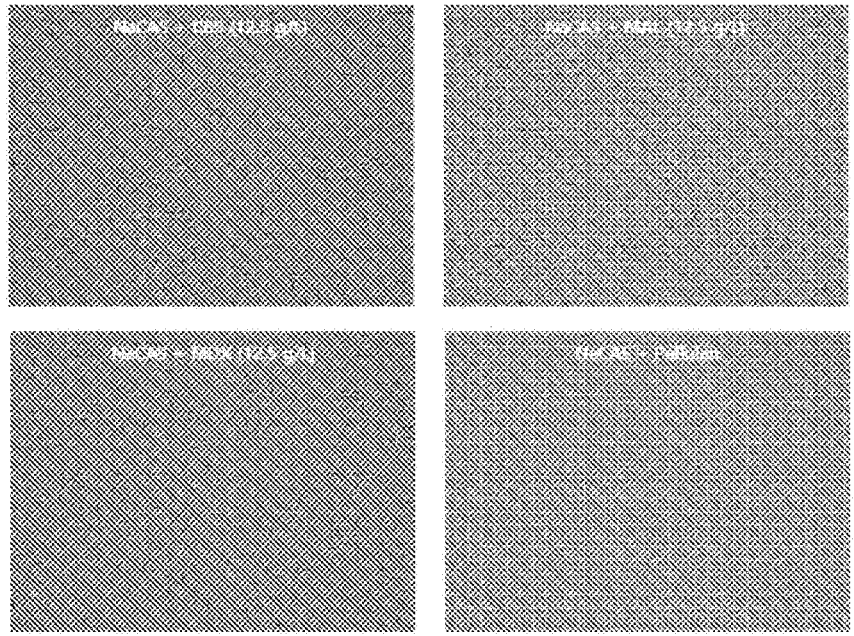
[FIG 8]
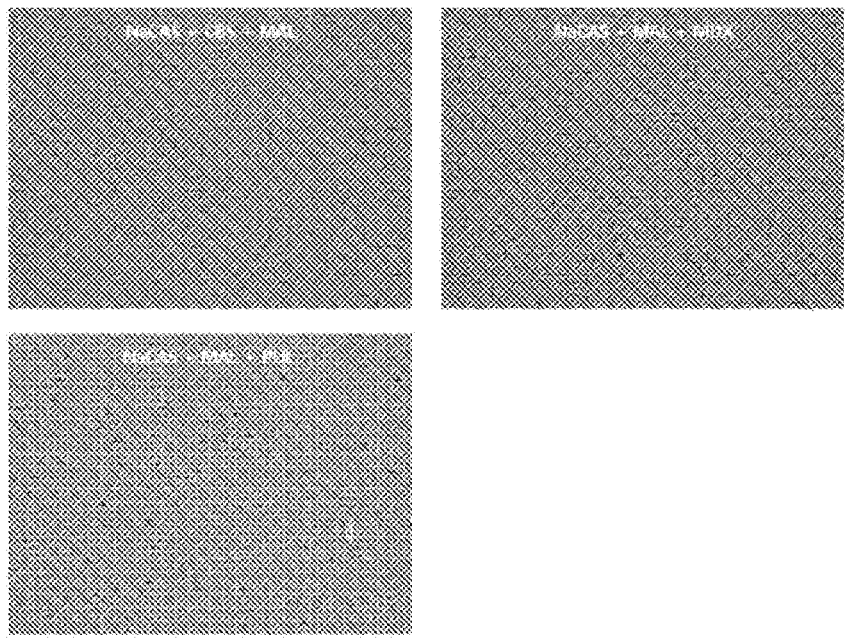

[FIG 9]
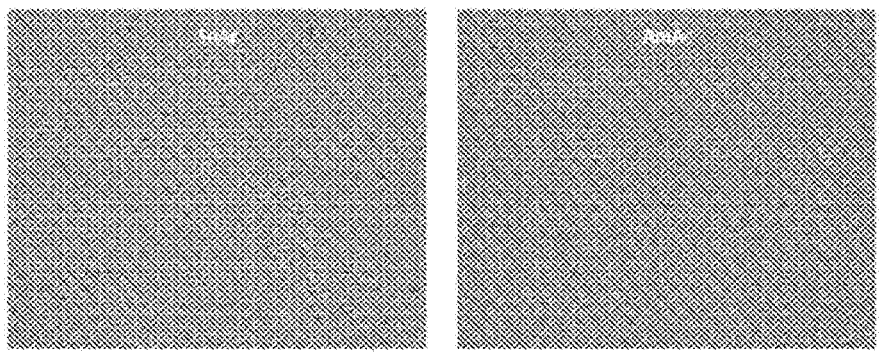
[FIG 10]
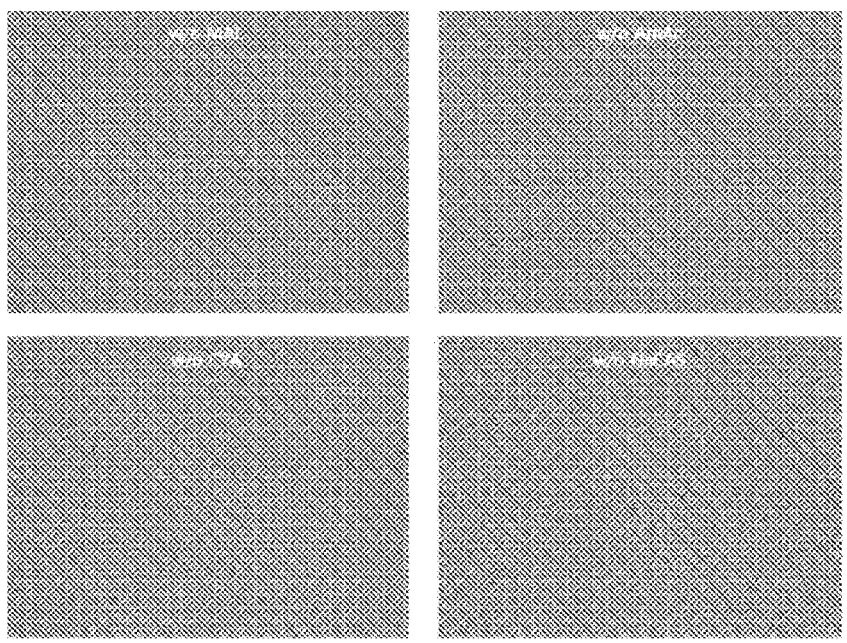

[FIG. 11]
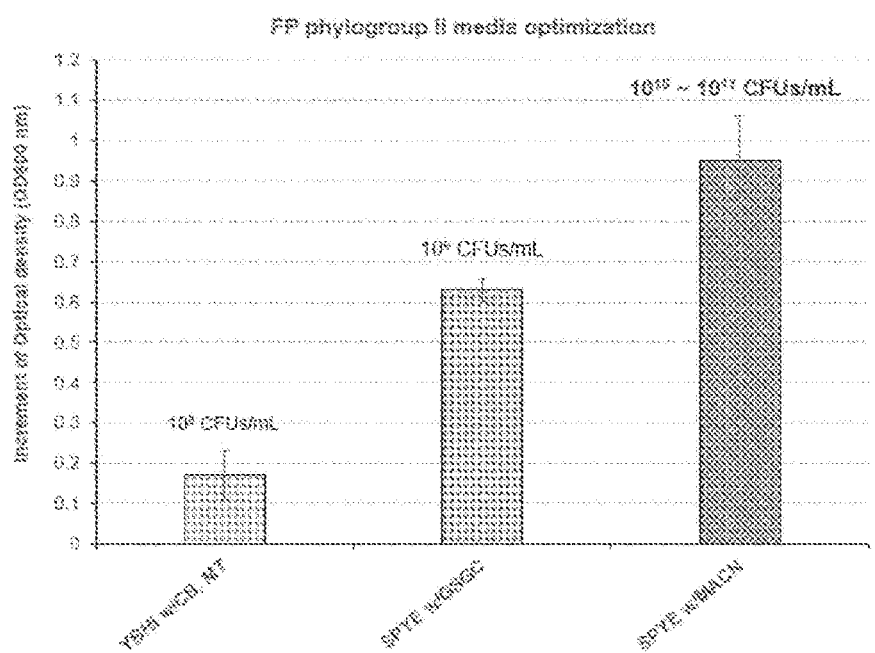

[FIG 1 2]
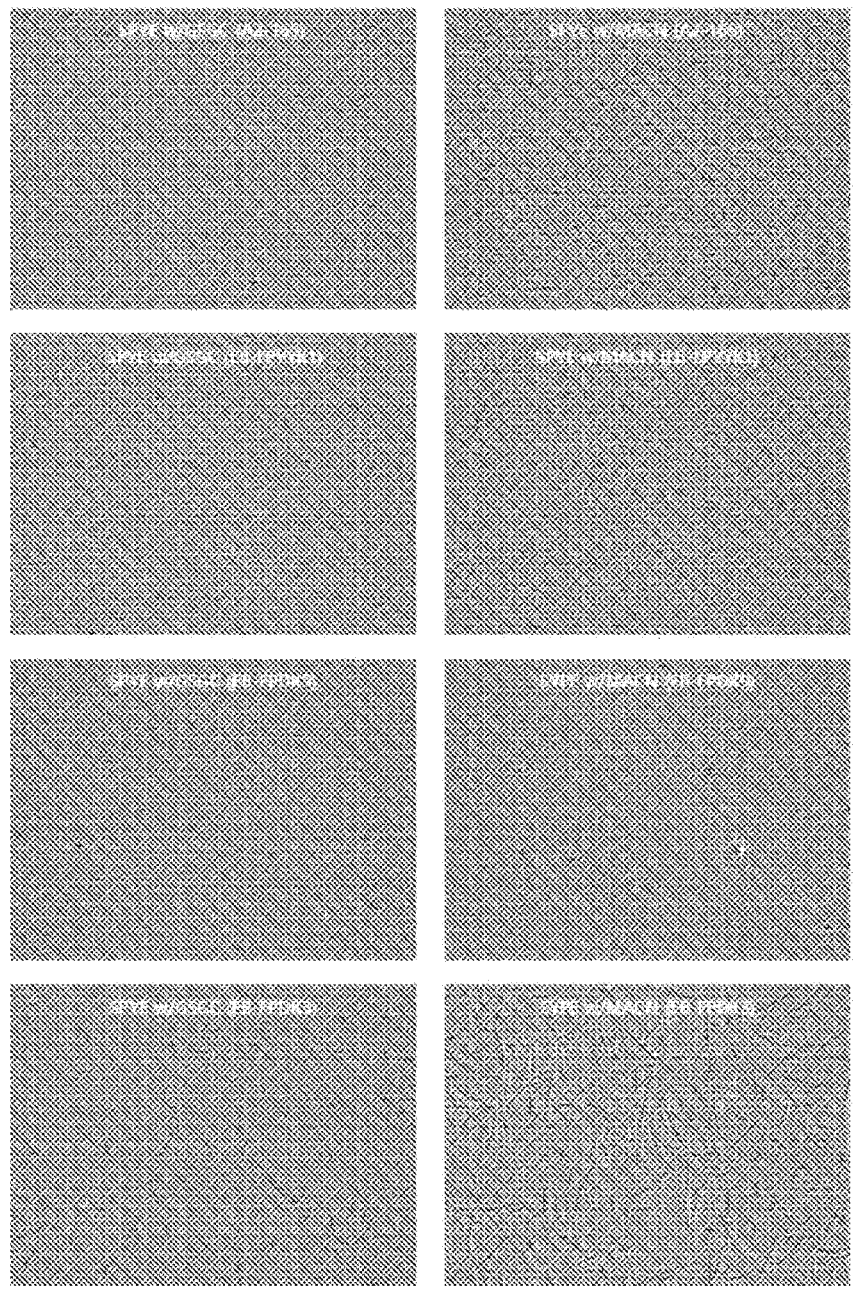

[FIG 1 3]
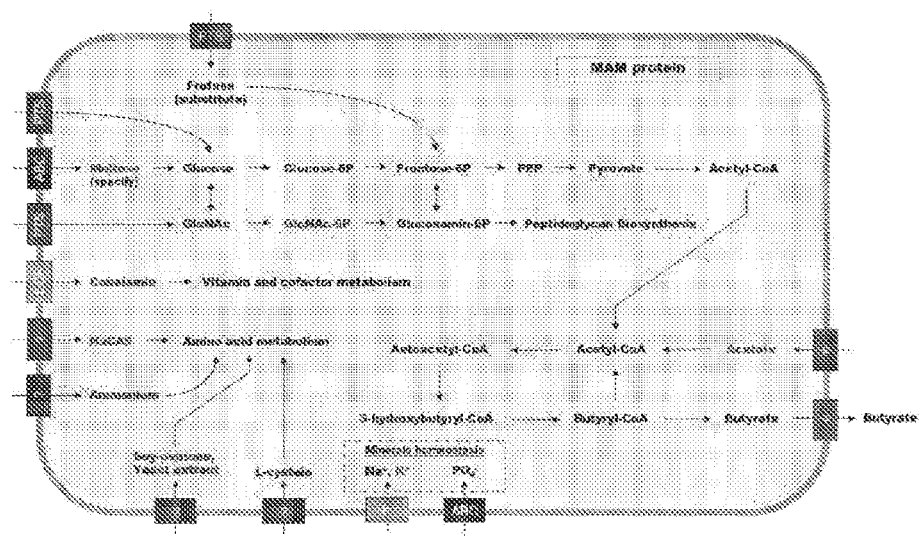

[FIG. 14A]
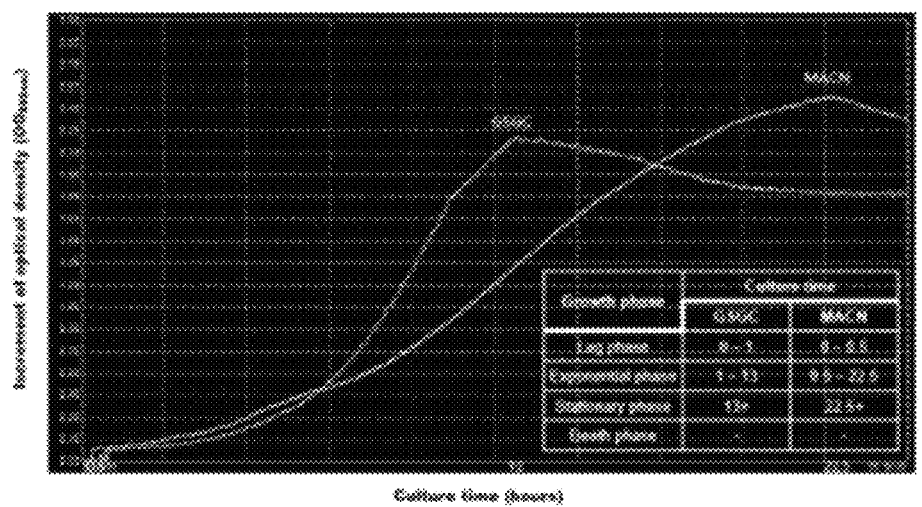
[FIG. 14B]
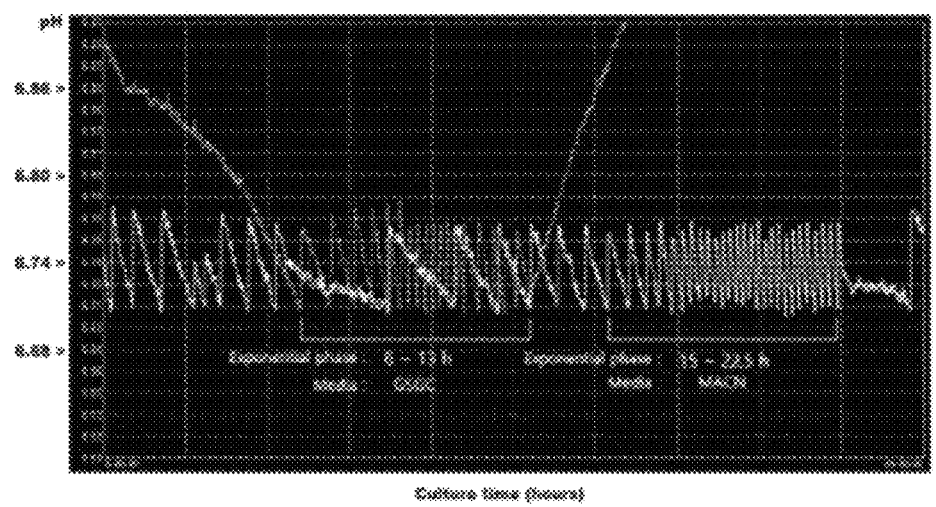

[FIG 15]
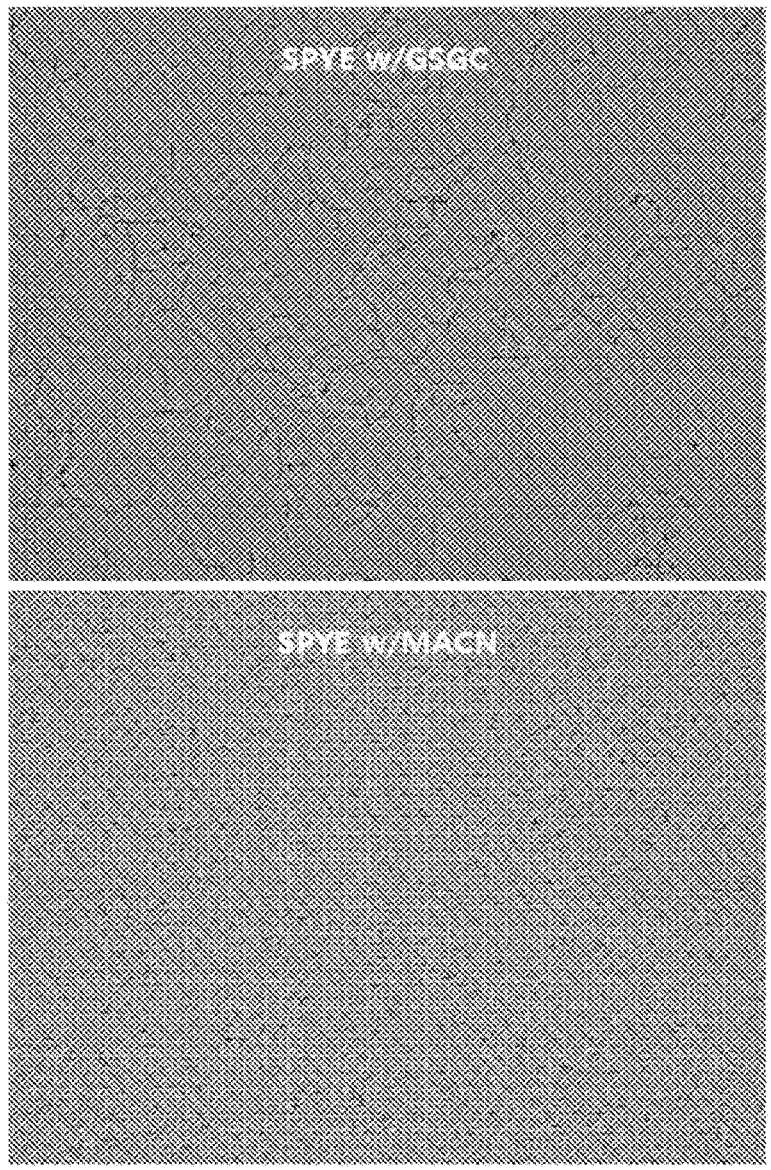

[Fig. 16]
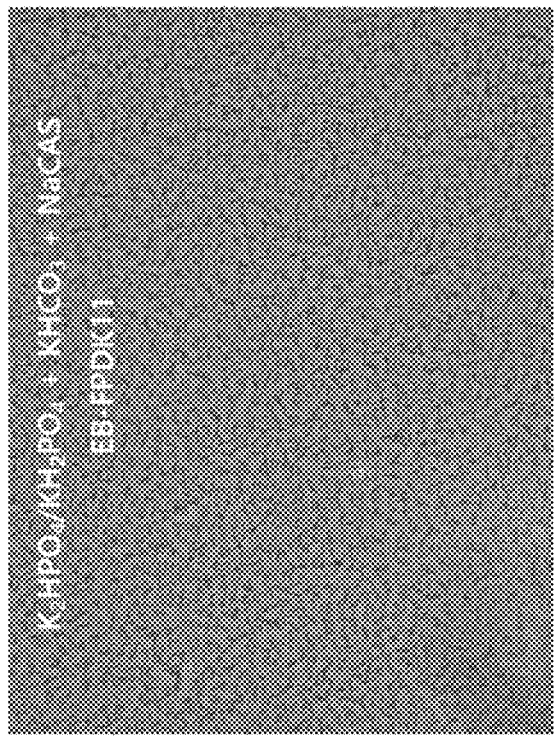
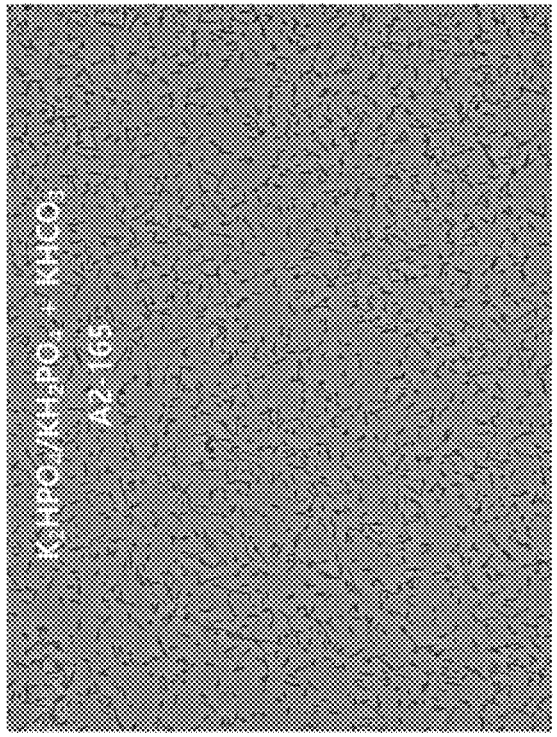
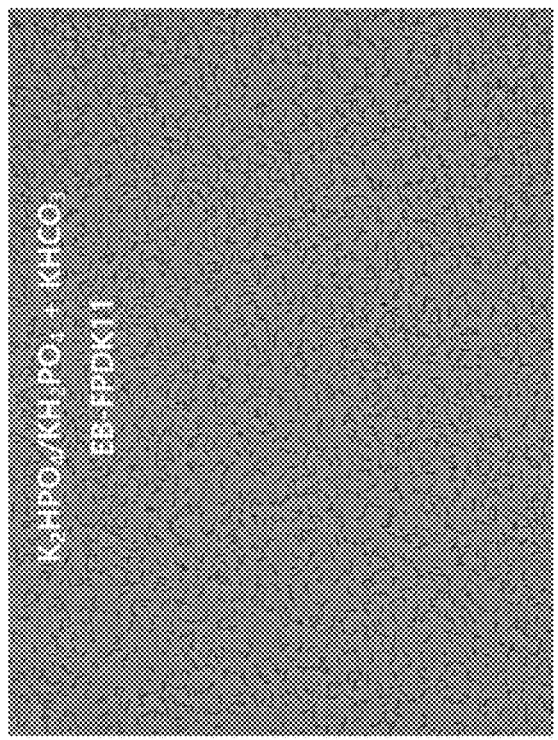
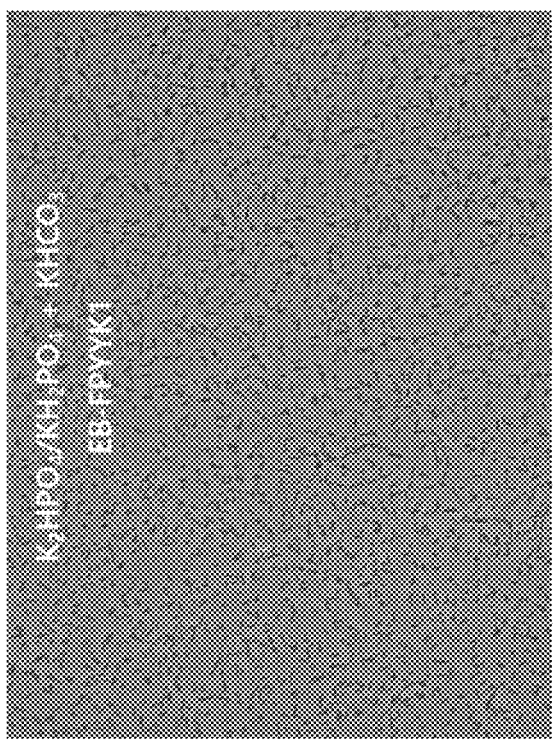

COMPOSITION OF CULTURE MEDIA FOR *FAECALIBACTERIUM PRAUSNITZII*

TECHNICAL FIELD

The present invention relates to a medium composition for culturing a *Faecalibacterium prausnitzii* strain.

BACKGROUND ART

*Faecalibacterium prausnitzii* is a butyrate-producing bacterium that is most widely distributed in the stomach and intestines, and it is very important to maintain the number of *Faecalibacterium prausnitzii* in the intestines at a certain level or higher. In fact, it was observed that the number of *Faecalibacterium prausnitzii* rapidly decreased in Crohn's disease patients and ulcerative colitis patients. Accordingly, it has been reported that *Faecalibacterium prausnitzii* is also involved in O-glycan formation in the mucus layer and has an important effect on the physiological function of the intestines. Thus, if such *Faecalibacterium prausnitzii* is mass-produced and taken, it will be possible to secure intestinal butyrate.

In recent studies focusing on the diversity of the genus *Faecalibacterium*, Lopez-Siles et al. analyzed the phylogenetic correlation of *Faecalibacterium prausnitzii* isolates based on the 16S rRNA gene sequences, and as a result, identified two different phylogroups I and II in *Faecalibacterium prausnitzii* species, and reported that the utilization of carbon sources (glucose, cellobiose, maltose, galacturonic acid, galactose, apple pectin, inulin, glucuronic acid, N-acetylglucosamine, etc.) is different between the phylogroups even within the same species (Lopez-Siles et al., Appl Environ Microbiol., 2012; 78:420-428).

It has been reported that *Faecalibacterium prausnitzii* species all possess β-galactosidase, α-glucosidase and phosphatase activities, but do not possess urease, arginine dihydrolase, β-glucosidase and α-fucosidase activities, and it was shown that the *Faecalibacterium prausnitzii* species could proliferate in YCFA media supplemented with fructose, fructo-oligosaccharides and glucose as substrates, but did not proliferate in YCFA media supplemented with arabinose, melibiose, raffinose, rhamnose, ribose and xylose (Duncan et al., 2002). Since the *Faecalibacterium prausnitzii* species have beta-galactosidase, which is an enzyme that converts lactose into galactose and glucose, and alpha-glucosidase which is an enzyme that converts maltose into glucose, carbon sources such as lactose and maltose are all can be used to form ATP, which is a high-energy molecule, through glycolysis.

Amino acids are important for maintaining the metabolic function of cells cultured in cell culture media, and external protein sources are essential to sustain good proliferation in high density culture. The amino acid source may be any known amino acid sources, and non-limiting examples thereof include an amino acid source derived from an animal, derived from a plant, or derived from a microorganism. The amino acid source may ideally be fully plant or microbial based. In addition, the amino acid source may be, for example, protein hydrolysates such as plant-derived protein hydrolysates. Protein hydrolysates are produced from protein sources using hydrolysis and are typically composed of a mixture of peptides, amino acids, carbohydrates and lipids, and a multitude of unidentified components with indeterminate biological activity. They are often produced by the enzymatic, alkaline or acidic digestion of a given raw material from various sources, such as, without limitation, plant sources (e.g., soy, wheat, pea, chickpea or cotton). The amino acid source may also be an amino acid composition containing an individual amino acid or a combination of individual amino acids.

The technology of culturing *Faecalibacterium prausnitzii* species currently remains at a level of $10^9$ CFUs/mL, which is an obstacle to the development of a mass production process, and culture of *Faecalibacterium prausnitzii* species at a high density of about $10^{11}$ CFUs/mL is expected to be a very important technology in the industrialization stage.

*Faecalibacterium prausnitzii* strains belonging to phylogroup II show cellular morphology significantly different from that of *Faecalibacterium prausnitzii* strains belonging to phylogroup I. In particular, it was confirmed that, when *Faecalibacterium prausnitzii* strains belonging to phylogroup II were cultured in media containing amino sugars such as N-acetyl-D-glucosamine (GlcNAc), they showed a long chain of rod-shaped cells. For this reason, there is a limit to increase the number of the cells in a limited space, and thus there is difficulty in culturing the cells at a high density of about $10^{11}$ CFUs/mL.

DISCLOSURE

Technical Problem

One aspect provides a medium composition for culturing *Faecalibacterium prausnitzii* composed of vegetable peptone, yeast extract, a phosphate compound, a carbonate compound, cyanocobalamin, L-cysteine, ammonium acetate, and maltose.

Another aspect provides a method for culturing *Faecalibacterium prausnitzii* comprising steps of: inoculating *Faecalibacterium prausnitzii* into the medium composition; and culturing the inoculated *Faecalibacterium prausnitzii* under conditions of a temperature of 35 to 38° C., a pH of 6.5 to 7, and a gas flow rate of 0.1 to 0.3 L/h.

Technical Solution

One aspect provides a medium composition for culturing *Faecalibacterium prausnitzii* composed of vegetable peptone, yeast extract, a phosphate compound, a carbonate compound, cyanocobalamin, L-cysteine, ammonium acetate, and maltose.

According to one embodiment, the carbonate compound may be present at a concentration of 2 to 6 g/L.

According to one embodiment, the maltose may be present at a concentration of 2.5 to 30 g/L.

According to one embodiment, the ammonium acetate may be present at a concentration of 2 to 16 g/L.

According to one embodiment, the *Faecalibacterium prausnitzii* may be *Faecalibacterium prausnitzii* phylogroup II.

Another aspect provides a method for culturing *Faecalibacterium prausnitzii* comprising steps of: inoculating *Faecalibacterium prausnitzii* into the medium composition; and culturing the inoculated *Faecalibacterium prausnitzii* under conditions of a temperature of 35 to 38° C., a pH of 6.5 to 7, and a gas flow rate of 0.1 to 0.3 L/h.

Advantageous Effects

When the medium composition and the method for culturing *Faecalibacterium prausnitzii* according to the present invention are used, high-density culture and mass production of strains of *Faecalibacterium prausnitzii* phylogroup II are possible. In addition, when *Faecalibacterium prausnitzii* is mass-cultured in the medium composition free of animal components, it may be cultured at high density even in high-concentration anaerobic nitrogen gas, and thus it is possible to provide a culture method which is more economical and suitable for industrialization.

BRIEF DESCRIPTION OF DRAWINGS

FIG. 1 shows micrographs of strains obtained by culturing *Faecalibacterium prausnitzii* with a combination of glucose (GlU) and N-acetylglucosamine (GlcNAc) or a combination of glucose (GlU) and a replacement component in order to find a component to replace N-acetylglucosamine (GlcNAc) (GLU: glucose, GlcNAc: N-acetylglucosamine, and NaCAS: sodium caseinate).

FIG. 2 shows micrographs of strains obtained by culturing *Faecalibacterium prausnitzii* with a combination of glucose (GlU) and N-acetylglucosamine (GlcNAc) or a combination of glucose (GlU) and a replacement component in order to find a component to replace N-acetylglucosamine (GlcNAc) (GLU: glucose, FOS: fructooligosaccharide, PEC: pectin, CEL: cellulose, CHI: chitin, and TRE: trehalose).

FIG. 3 shows micrographs of strains obtained by culturing *Faecalibacterium prausnitzii* in a medium composed of sodium caseinate and each carbon source (NaCAS: sodium caseinate, FRU: fructose, GAL: galactose, LAC: lactose, CBS: cellobiose, MAL: maltose, and SPV: sodium pyruvate).

FIGS. 4A and 4B show the maltose uptake control process disclosed in the literature "An integrated transport mechanism of the maltose ABC importer (Machtel et al., 2019, Res. Microbiol., 190: 321-337.)". FIG. 4A shows a process in which PTS sugar employing a transporter is present and maltose uptake is repressed by PTS permease activity, and FIG. 4B shows a process in which PTS sugar is absent and maltose uptake is activated while PTS permease is not activated.

FIG. 5 depicts data which show the results of analyzing the genomes of *Faecalibacterium prausnitzii* strains, and which indicate that the copy number of the ABC transporter-related gene is larger in phylogroup II (A2-165, EB-FPDK11, and EB-FPYYK1) than in phylogroup I (ATCC27768, EB-FPDK9) and the unclassified group (EB-FPDK3).

FIG. 6 depicts data showing the similarity between the genomes of strains based on average nucleotide identity (ANI).

FIG. 7 shows micrographs of strains obtained by culturing *Faecalibacterium prausnitzii* in media supplemented with sodium caseinate and cellobiose (CBS), maltose (MAL), maltodextrin (MDX) or pullulan (PUL).

FIG. 8 shows micrographs of strains obtained by culturing *Faecalibacterium prausnitzii* in media containing sodium caseinate (NaCAS)+cellobiose (CBS)+maltose (MAL), sodium caseinate (NaCAS)+maltose (MAL)+maltodextrin (MDX), or sodium caseinate (NaCAS)+maltose (MAL)+pullulan (PUL).

FIG. 9 shows micrographs comparing the appearance of *Faecalibacterium prausnitzii* cultured in a medium supplemented with sodium acetate (SoAc) with the appearance of *Faecalibacterium prausnitzii* cultured in a medium supplemented with ammonium acetate (AmAc).

FIG. 10 shows micrographs of *Faecalibacterium prausnitzii* cultured in media free of any one of maltose (MAL), ammonium acetate (AmAc), cyanocobalamin (CYA), and sodium caseinate (NaCAS).

FIG. 11 shows data which indicates that *Faecalibacterium prausnitzii* was cultured at high density in the medium of the present invention, and which compare the viable cell count of *Faecalibacterium prausnitzii* cultured in the medium of the present invention with the viable cell count number of *Faecalibacterium prausnitzii* cultured in either a YBHI w/CB, MT medium (unoptimized) disclosed in Korean Patent No. 10-2245415 or a SPYE w/GSGC medium (containing soy-peptone, yeast extract, glucose, dipotassium phosphate, GlcNAc, sodium acetate, and cyanocobalamin and pretreated with 0.05% w/v L-cysteine; hereinafter referred to as "SPYE w/GSGC medium").

FIG. 12 shows micrographs of strains obtained by culturing *Faecalibacterium prausnitzii* phylogroup II strains (A2-165, and EB-FPYYK1), a *Faecalibacterium prausnitzii* phylogroup I strain (EB-FPDK9) and a *Faecalibacterium prausnitzii* unclassified group strain (EB-FPDK3) in the SPYE w/GSGC medium or a SPYE w/MACN medium (containing soy-peptone, yeast extract, dipotassium phosphate, maltose, ammonium acetate, cyanocobalamin, and sodium caseinate and pretreated with 0.05% w/v L-cysteine; hereinafter referred to as "SPYE w/MACN medium").

FIG. 13 shows an expected process in which the medium composition of the present invention is metabolized in *Faecalibacterium prausnitzii*.

FIG. 14A depicts data showing the OD value depending on the culture time in the SPYE w/GSGC or SPYE w/MACN medium.

FIG. 14B depicts data showing the pH value depending on the culture time in the SPYE w/GSGC or SPYE w/MACN medium.

FIG. 15 shows micrographs of strains obtained by mass culture in the SPYE w/GSGC or SPYE w/MACN medium composition.

FIG. 16 shows micrographs obtained after culturing *Faecalibacterium prausnitzii* phylogroup II strains (EB-FPDK11, EB-FPYYK1, and A2-165) in media containing phosphate and carbonate.

BEST MODE

One aspect provides a medium composition for culturing *Faecalibacterium prausnitzii* composed of vegetable peptone, yeast extract, a phosphate compound, a carbonate compound, cyanocobalamin (B12), L-cysteine, ammonium acetate, and maltose.

The soy peptone and the yeast extract may be plant- or microorganism-derived components that replace animal components. Animal-derived components may contain contaminants of viral or bacterial origin or may contain allergens or antigenic peptides. Thus, these animal-derived components are unsuitable for use as biopharmaceuticals and health functional foods, and thus may be replaced with the plant- or microorganism-derived components.

The vegetable peptone may be a peptone extracted from a plant, and examples thereof include, but are not limited to, soy peptone, wheat peptone, cotton peptone, pea peptone, broadbean peptone, lupin peptone, and potato peptone. The vegetable peptone may be contained in the medium composition in an amount of 10 g/L to 20 g/L or 15 g/L to 20 g/L.

The yeast extract may serve as a protein source in a non-animal medium and to further increase the proliferation of anaerobic microorganisms. The yeast extract may be yeast autolysate, ultrafiltered yeast extract or synthetic yeast extract. The yeast extract may be present at a concentration of 5 g/L to 10 g/L, for example, 10 g/L.

The phosphate compound may be disodium phosphate ($Na_2HPO_4$), dipotassium phosphate ($K_2HPO_4$) or potassium phosphate ($KH_2PO_4$). The phosphate compound may be a substance which is added to the cell culture medium to maintain isotonic conditions and prevent osmotic imbalance. The medium composition of the present invention may preferably be maintained in a pH range of 6.5 to 8.0, 6.0 to 7.0, or 5.8 to 7.8, but is not limited thereto.

According to one embodiment, the carbonate compound may be present at a concentration of 2 to 6 g/L, for example, 2 to 4 g/L, 2 to 5 g/L, 3 to 4 g/L, 3 to 5 g/L, 3 to 6 g/L, 4 to 5 g/L, or 4 to 6 g/L.

The carbonate compound may be a component that acts as a buffer together with the phosphate compound, and may be a component that increases economic feasibility during mass culture by producing $CO_2$.

According to one embodiment, the maltose may be present at a concentration of 2.5 to 30 g/L, for example, 2.5 to 25 g/L, 2.5 to 20 g/L, 2.5 to 15 g/L, or 2.5 to 12.5 g/L.

According to one embodiment, the ammonium acetate may be present at a concentration of 2 to 16 g/L, for example, 2 to 16 g/L, 2 to 12 g/L, 2 to 10 g/L, 4 to 16 g/L, 4 to 12 g/L, or 4 to 10 g/L.

Microbial culture conditions may affect the growth rate of the microorganism, as is well known by those skilled in the art. In the present invention, the culturing step may be performed at a pH of 6.6 to 7.0, a culture temperature of 36° C. to 39° C., an agitation speed of 40 rpm to 50 rpm, a nitrogen saturation of 80% to 100%, a hydrogen saturation of 0% to 5%, and a carbon dioxide saturation of 0% to 20%.

The term "*Faecalibacterium prausnitzii*" includes all phylogroups I, IIa and IIb of *Faecalibacterium prausnitzii*, including, for example, but not limited to, *Faecalibacterium prausnitzii* EB-FPDK9 of phylogroup I, *Faecalibacterium prausnitzii* A2-165 and *Faecalibacterium prausnitzii* EB-FPYYK1 of phylogroup IIa, *Faecalibacterium prausnitzii* EB-FPDK11 of phylogroup IIb, and *Faecalibacterium prausnitzii* EB-FPDK3 of the unclassified group.

According to one embodiment, the *Faecalibacterium prausnitzii* may be *Faecalibacterium prausnitzii* phylogroup II. For example, it may be *Faecalibacterium prausnitzii* EB-FPDK11.

Another aspect provides a method for culturing *Faecalibacterium prausnitzii* comprising steps of: inoculating *Faecalibacterium prausnitzii* into the medium composition of the present invention; and culturing the inoculated *Faecalibacterium prausnitzii* under conditions of a temperature of 35 to 38° C., a pH of 6.5 to 7, and a gas flow rate of 0.1 to 0.3 L/h.

Details regarding the *Faecalibacterium prausnitzii* are the same as described above.

MODE FOR INVENTION

Hereinafter, one or more specific embodiments will be described in more detail with reference to examples. However, these examples serve to illustrate one or more embodiments, and the scope of the present invention is not limited to these examples.

Example 1. Examination of Changes in Cellular Morphology Depending on Medium Supplements Changes in the cellular morphology of a *Faecalibacterium prausnitzii* phylogroup II strain in culture media supplemented with various substrates known in the existing literatures (Duncan et al., 2002; Lopez-Siles et al., 2012, and Lopez-Siles et al., 2017) with respect to *Faecalibacterium prausnitzii* culture were examined.

As the *Faecalibacterium prausnitzii* phylogroup II strain, *Faecalibacterium prausnitzii* EB-FPDK11 (accession number: KCCM12621P) disclosed in Korean Patent No. 10-2169794 was used.

The medium composition disclosed in Korean Patent No. 10-2245415 is a medium composition (hereinafter referred to as "SPYE w/GSGC" medium composition) containing 20 g/L soy-peptone, 10 g/L yeast extract, 2.5 g/L glucose, 2.5 g/L dipotassium phosphate, 2.5 g/L N-acetyl-D-glucosamine (GlcNAc), 2 g/L sodium acetate, and 0.1 mg/L cyanocobalamin ($B_{12}$) and pretreated with 0.05% w/v L-cysteine. The culturability of the strain in the medium composition was analyzed comparatively with that of the strain in the SPYE w/GSGC medium composition.

To this end, the *Faecalibacterium prausnitzii* EB-FPDK11 isolate was inoculated into each prepared medium at a ratio of 0.1% v/v, and then the change in turbidity (OD 600 nm) was measured while the inoculated isolate was cultured at 37° C. under anaerobic conditions (90% $N_2$, 5% $CO_2$, and 5% $H_2$) for 24 to 48 hours. The SPYE medium described below is a medium containing 20 g/L soy-peptone, 10 g/L yeast extract, 2.5 g/L dipotassium phosphate, 2 g/L sodium acetate, and 0.1 mg/L cyanocobalamin ($B_{12}$), and pretreated with 0.05% w/v L-cysteine. As shown in Table 1 below, media composed of a combination of two or more of glucose (Glu), N-acetyl glucosamine (GlcNAc), sodium caseinate (NaCAS), fructooligosaccharide (FOS), pectin (PEC), cellulose (CEL), chitin (CHI) and trehalose (TRE) were prepared, and the turbidity of each medium and the cellular morphology were examined.

TABLE 1

| Basal medium | GLU | GlcNAc | NaCAS | FOS | PEC | CEL | CHI | TRE | Growth (ΔOD$_{600}$) | Cellular morphology |
|---|---|---|---|---|---|---|---|---|---|---|
| SPYE | 2.5 | 2.5 | — | — | — | — | — | — | 0.583 ± 0.007 | Long and twisted |
|  | 2.5 | 2.5 | 2.5 | — | — | — | — | — | 0.685 ± 0.027 | rods, in chains |
|  | 2.5 | — | — | — | — | — | — | — | 0.448 ± 0.020 | Shorter and |
|  | 2.5 | — | 2.5 | — | — | — | — | — | 0.487 ± 0.007 | straight rods, |
|  | 2.5 | — | 2.5 | 2.5 | — | — | — | — | 0.413 ± 0.009 | in chains |
|  | 2.5 | — | 2.5 | — | 2.5 | — | — | — | 0.437 ± 0.001 |  |
|  | 2.5 | — | 2.5 | — | — | 2.5 | — | — | 0.437 ± 0.001 |  |
|  | 2.5 | — | 2.5 | — | — | — | 2.5 | — | 0.456 ± 0.024 |  |
|  | 2.5 | — | 2.5 | — | — | — | — | 2.5 | 0.427 ± 0.023 |  |

As can be seen in Table 1 above and FIGS. 1 and 2, it was confirmed that the *Faecalibacterium prausnitzii* EB-FPDK11 strain showed a relatively short and straight cellular morphology in the media not supplemented with GlcNAc, and the absorbance was slightly lowered in these media, but there was no significant change in cell density (cell number). In addition, as can be seen from the results for the media supplemented with sodium caseinate (NaCAS), it was confirmed that sodium caseinate could somewhat compensate for the reduction in culturability that did occur when the media were not supplemented with N-acetylglucosamine (GlcNAc).

Example 2. Identification of Optimal Combination of Carbon Sources

In order to identify optimal carbon sources when using sodium caseinate (NaCAS) as a substitute for N-acetylglucosamine (GlcNAc) in the SPYE medium, glucose (GLU), fructose (FRU), galactose (GAL), lactose (LAC), cellobiose (CBS), maltose (MAL) and sodium pyruvate (SPV) were combined as shown in Table 2 below, and culturability was examined.

and size decreased, the absorbance decreased, but the cell density (cell number) did not greatly change.

Maltose employs an ABC transporter, and it can be seen through FIG. 4, which is an excerpt from the literature "An integrated transport mechanism of the maltose ABC importer (Machtel et al., 2019, Res. Microbiol., 190: 321-337)", that when sugars (PTS sugar: glucose, fructose, GlcNAc, etc.) are present, maltose uptake is repressed by PTS permease activity.

In addition, as shown in FIGS. 5 and 6, it was confirmed through analysis of the genomes of *Faecalibacterium prausnitzii* strains that the copy number of the ABC transporter-related gene was relatively larger in strains (A2-165, EB-FPDK11, and EB-FPYYK1) of phylogroup II than in strains (ATCC27768, and EB-FPDK9) of phylogroup I and EB-FPDK3 of the unclassified group, suggesting that substrates such as maltose may be useful for culture.

TABLE 2

| Basal medium | GlcNAc | NaCAS | GLU | FRU | GAL | LAC | CBS | MAL | SPV | Growth ($\Delta OD_{600}$) | Cellular morphology |
|---|---|---|---|---|---|---|---|---|---|---|---|
| SPYE | — | 2.5 | 2.5 | — | — | — | — | — | — | 0.487 ± 0.007 | Shorter and straight rods, in chains |
|  | — | 2.5 | — | 2.5 | — | — | — | — | — | 0.526 ± 0.025 |  |
|  | — | 2.5 | — | — | 2.5 | — | — | — | — | 0.367 ± 0.002 |  |
|  | — | 2.5 | — | — | — | 2.5 | — | — | — | 0.383 ± 0.016 |  |
|  | — | 2.5 | — | — | — | — | 2.5 | — | — | 0.433 ± 0.010 | Short and small rods |
|  | — | 2.5 | — | — | — | — | — | 2.5 | — | 0.155 ± 0.002 |  |
|  | — | 2.5 | — | — | — | — | — | — | 2.5 | 0.120 ± 0.002 | Twisted rods |

As shown in Table 2 above and FIG. 3, it was confirmed that, when glucose in the medium not containing N-acetylglucosamine was replaced with cellobiose or maltose, the cellular morphology was a very short rod shape, and in particular, when glucose in the medium was replaced with maltose, the cellular morphology was a very small rod shape, indicating the possibility of high-density culture in which the number of cells in a limited space can increase. Similarly, it was confirmed that, as the cellular morphology

Example 3. Examination of Whether Culturability is Improved Depending on Culture Concentration The SPYE medium was supplemented with various concentrations of not only maltose which showed a high possibility of high-density culture in the above-described Example, but also maltodextrin (MDX), pullulan (PUL) and cellobiose (CBS), which are polymers, and whether culturability would be improved was examined.

TABLE 3

| Basal medium | GlcNAc | NaCAS | GLU | CBS | MAL | MDX | PUL | Growth ($\Delta OD_{600}$) | Cellular morphology |
|---|---|---|---|---|---|---|---|---|---|
| SPYE | — | 2.5 | — | 2.5 | — | — | — | 0.433 ± 0.010 | Short rods, singly and rarely in chains |
|  | — | 2.5 | — | 7.5 | — | — | — | 0.498 ± 0.009 |  |
|  | — | 2.5 | — | 12.5 | — | — | — | 0.504 ± 0.012 |  |
|  | — | 2.5 | — | — | 2.5 | — | — | 0.155 ± 0.002 | Short and small rods, singly and rarely in chains |
|  | — | 2.5 | — | — | 7.5 | — | — | 0.449 ± 0.012 |  |
|  | — | 2.5 | — | — | 12.5 | — | — | 0.493 ± 0.009 |  |
|  | — | 2.5 | — | — | 25 | — | — | 0.510 ± 0.010 |  |
|  | — | 2.5 | — | — | 37.5 | — | — | 0.470 ± 0.008 |  |
|  | — | 2.5 | — | — | — | 2.5 | — | 0.152 ± 0.006 | Short rods, singly and rarely in chains |
|  | — | 2.5 | — | — | — | 7.5 | — | 0.228 ± 0.010 |  |
|  | — | 2.5 | — | — | — | 12.5 | — | 0.473 ± 0.014 |  |
|  | — | 2.5 | — | — | — | 25 | — | 0.454 ± 0.022 |  |
|  | — | 2.5 | — | — | — | — | 2.5 | 0.060 ± 0.003 | Short and small rods, singly and rarely in chains |
|  | — | 2.5 | — | — | — | — | 5 | 0.058 ± 0.001 |  |
|  | — | 2.5 | — | — | — | — | 7.5 | 0.058 ± 0.002 |  |
|  | — | 2.5 | — | 2.5 | 2.5 | — | — | 0.520 ± 0.006 | Short rods |
|  | — | 2.5 | — | — | 2.5 | 2.5 | — | 0.535 ± 0.005 | Short and small rods |
|  | — | 2.5 | — | — | 2.5 | — | 2.5 | 0.468 ± 0.013 | Twisted rods |

As shown in Table 3 above and FIGS. 7 and 8, it was confirmed that, when glucose in the medium not containing N-acetylglucosamine was replaced with maltose, the cellular morphology was a very short rod shape, and the absorbance greatly increased in a manner dependent on the concentration of maltose and was equivalent to that in the conventional medium (SPYE w/GSGC) at a maltose concentration of 12.5 g/L to 25 g/L, and particularly, as a result of microscopic observation, the cell density (cell number) significantly increased.

In addition, it was confirmed that, when the SPYE medium was supplemented with cellobiose or maltodextrin, the cellular morphology was a slightly longer rod shape than when the SPYE medium was supplemented with maltose alone, and when the SPYE medium was supplemented with pullulan, the cellular morphology was very short similar to when the medium was supplemented with maltose, but the absorbance and cell density were significantly low, suggesting that the SPYE medium supplemented with pullulan is not suitable as a culture medium for Faecalibacterium prausnitzii.

Example 4. Improvement in Culturability by Supplementation of Ammonium Acetate

The acetate of sodium acetate (SoAc) supplemented to a conventional medium is used as a substrate for producing butyrate and is known as a growth factor. In addition, N-acetylglucosamine is used for cell wall synthesis (peptidoglycan biosynthesis) and energy metabolism, and produces ammonia in the metabolic process, and the ammonia serves as a pH buffer to neutralize the cytoplasm, and functions as a nitrogen source. Thus, it was confirmed that the maltose medium free of N-acetylglucosamine was quite sensitive to pH changes, and the pH of the medium after culture was usually 6.1 to 6.3. It was confirmed that, when the pH in the maltose medium decreased to 6 or less, the cellular morphology changed and the culturability was not good. Thus, instead of sodium acetate, ammonium acetate (AmAc) was supplemented as a growth factor capable of providing a nitrogen source and an acetate salt while acting as a pH buffer, and whether culturability would be improved was examined. In order to examine whether culturability would be improved, a medium (hereinafter referred to as "SPYE w/MCN") containing the following components on the basis of the results of the above Examples and pretreated with 0.05% w/v L-cysteine was used as a basal medium: 20 g/L soy-peptone, 10 g/L yeast extract, 2.5 g/L dipotassium phosphate, 12.5 g/L maltose, 2.5 g/L sodium caseinate, and 0.1 mg/L cyanocobalamin ($B_{12}$).

As can be seen in Table 4 above and FIG. 9, it was confirmed that, in the media supplemented with ammonium acetate instead of sodium acetate, culturability increased in a manner dependent on the concentration of ammonium acetate, and particularly, the absorbance was the highest at an ammonium acetate concentration of 6 g/L, the cellular morphology was a very short rod shape, and the cell density (cell number) greatly increased. In addition, it was confirmed that, in the media supplemented with ammonium acetate at a concentration of 10 g/L or higher, culturability decreased rather than increased, and in the medium supplemented with ammonium acetate at a concentration of 20 g/L, cells could not proliferate.

Example 5. Evaluation of Importance of Each Medium Supplement

The effect of each component in a combination of the above-suggested substrates (maltose, ammonium acetate, cyanocobalamin, and sodium caseinate) on culture was evaluated.

TABLE 5

| Basal medium | Supplements (g/L) | | | | Growth ($\Delta OD_{600}$) |
|---|---|---|---|---|---|
|  | MAL | AmAc | CYA | NaCAS |  |
| SPYE | 12.5 | 6 | 0.1 | 2.5 | 0.958 ± 0.035 |
|  | — | 6 | 0.1 | 2.5 | 0.046 ± 0.001 |
|  | 12.5 | — | 0.1 | 2.5 | 0.095 ± 0.003 |
|  | 12.5 | 6 | — | 2.5 | 0.186 ± 0.011 |
|  | 12.5 | 6 | 0.1 | — | 0.526 ± 0.010 |

As can be seen from Table 5 above and FIG. 10, it was confirmed that, when even one of the four supplements was excluded, culturability significantly decreased, and as a result of microscopic observation, the cell density (cell number) also significantly decreased.

Example 6. Evaluation of Improvement in Culturability of Phylogroup II Strains

Whether the culturability of different strains of Faecalibacterium prausnitzii phylogroup II in the optimized medium determined through Example 5 would be improved was evaluated. For comparison of the effect, the EB-FPDK9 strain of phylogroup I and the EB-FPDK3 strain that does not belong to phylogroups I and II were used.

TABLE 4

| Basal medium | Supplements (g/L) | | Growth ($\Delta OD_{600}$) | Cellular morphology | VCC (CFUs/mL) |
|---|---|---|---|---|---|
|  | SoAc | AmAc |  |  |  |
| SPYE w/MCN | 2 | — | 0.493 ± 0.009 | Short and small rods | 2.8 × 10$^{10}$ |
|  | — | 2 | 0.475 ± 0.007 | Short and small rods, singly and rarely in pairs | ND |
|  | — | 4 | 0.556 ± 0.007 |  | ND |
|  | — | 6 | 0.958 ± 0.035 |  | 1.47 × 10$^{11}$ |
|  | — | 10 | 0.653 ± 0.010 |  | ND |
|  | — | 16 | 0.552 ± 0.024 |  | ND |
|  | — | 20 | 0.008 ± 0.002 |  | ND |

TABLE 6

| Phylogroup | Tested strains | Media | Growth ($\Delta OD_{600}$) | Morphological changes | VCC (CFUs/mL) |
|---|---|---|---|---|---|
| II | EB-FPDK11 | SPYE w/GSGC | 0.589 ± 0.003 | Yes (shorter rods) | $2.0 \times 10^9$ |
|  |  | SPYE w/MACN | 0.958 ± 0.035 |  | $1.5 \times 10^{11}$ |
|  | EB-FPYYK1 | SPYE w/GSGC | 0.600 ± 0.025 |  | $2.0 \times 10^9$ |
|  |  | SPYE w/MACN | 0.909 ± 0.051 |  | $1.5 \times 10^{10}$ |
|  | A2-165 | SPYE w/GSGC | 0.655 ± 0.032 |  | $3.0 \times 10^9$ |
|  |  | SPYE w/MACN | 1.057 ± 0.030 |  | $3.3 \times 10^{10}$ |
| I | EB-FPDK9 | SPYE w/GSGC | 0.663 ± 0.006 | None | ND |
|  |  | SPYE w/MACN | 0.786 ± 0.006 |  | ND |
| Unclassified | EB-FPDK3 | SPYE w/GSGC | 0.402 ± 0.021 | None | ND |
|  |  | SPYE w/MACN | 1.164 ± 0.024 |  | ND |

As shown in Table 6 above and FIG. 11, it was confirmed that, according to the present invention, it was possible to culture the strains of *Faecalibacterium prausnitzii* phylogroup II at a high density of $10^{10}$ to $10^{11}$ CFUs/mL by using the SPYE w/MACN medium (composed of a combination of 20 g/L soy-peptone, 10 g/L yeast extract, 2.5 g/L dipotassium phosphate, 12.5 g/L maltose, 6 g/L ammonium acetate, 0.1 mg/L cyanocobalamin and 2.5 g/L sodium caseinate).

In addition, as shown in FIG. 12, as a result of microscopic observation, it was confirmed that A2-165 and EB-FPYYK1 of *Faecalibacterium prausnitzii* phylogroup II showed a shorter cellular morphology and a higher cell density in the SPYE w/MACN medium than in the SPYE/GSGC medium. On the other hand, it was confirmed that, in the SPYE w/MACN medium, EB-FPDK9 of *Faecalibacterium prausnitzii* phylogroup I and EB-FPDK3 of the unclassified group showed no significant difference in culturability from those in the SPYE/GSGC medium or grew longer, suggesting that these strains cannot be cultured at high density in the SPYE w/MACN medium.

Through the present invention, it is expected that medium components, which are a combination of soy peptone, yeast extract, maltose, ammonium acetate, cyanocobalamin and sodium caseinate, will be metabolized in *Faecalibacterium prausnitzii* through the metabolic pathway shown in FIG. 13, and will also increase economic feasibility by replacing expensive N-acetylglucosamine.

Example 7. Examination of Whether Mass Culture is Possible

Using a customized anaerobic fermenter system that can identify and maintain anaerobic conditions for culturing extremely oxygen sensitive (EOS) strains such as *Faecalibacterium prausnitzii*, mass culture at a 3-liter fermentation scale in the medium composition (Table 6) established above was implemented. To this end, culture was carried out in the medium composition shown in Table 7 below under the conditions shown in Table 8 below, and changes in the growth curve and pH were checked. In addition, morphological changes were examined through microscopic observation, and the viable cell count of the cultured strain was measured using the plate counting method.

TABLE 7

| Approximate Formula Per Liter of Purified Water | |
|---|---|
| Soy-peptone | 20.0 g |
| Yeast extract | 10.0 g |
| Dipotassium phosphate | 2.5 g |

TABLE 7-continued

| Supplements | |
|---|---|
| D-Maltose | 12.5 g |
| Ammonium acetate | 6.0 g |
| Cyanocobalamin | 0.1 mg |
| Sodium caseinate | 2.5 g |
| L-cysteine · HCl anhydrous | 0.5 g |
| DI water | 1 L |

Solution is dark brown, slightly hazy.

TABLE 8

| | |
|---|---|
| Temperature (° C.) | 37 ± 1 |
| pH | 6.8 ± 0.2 |
| Gas flow (100% $N_2$ or 90% $N_2$, 5% $CO_2$, and 5% $H_2$) | 0.2 liters/h |
| Agitation speed | 40 to 50 rpm |
| Inoculum | 1% v/v |
| Working volume | 3 L |

As a result, as shown in FIG. 14, it was confirmed that the *Faecalibacterium prausnitzii* EB-FPDK11 strain reached the highest absorbance within 22.5 hours in mass culture performed using the fermenter, the absorbance (OD600) at this time was 1.23, which was equivalent in test tube culture and was at least two times higher than that in the medium (SPYE w/GSGC) disclosed in Korean Patent No. 10-2245415, and the viable cell count of the strain cultured in the medium composition of the present invention was $2.0 \times 10^{11}$ CFUs/mL, which was 100-fold larger than the viable cell count of the strain cultured in the SPYE w/GSGC medium ($2.04 \times 10^9$ CFUs/mL). As a result of microscopic observation, as shown in FIG. 15, it was confirmed that the cells cultured in the SPYE w/MACN medium showed a very short and small rod cellular morphology compared to the cells cultured in the SPYE w/GSGC medium, and the cell density (cell number) also significantly increased in the SPYE w/MACN medium.

Example 8. Identification of Culture Conditions in Consideration of Efficiency and Economic Feasibility of Mass Production It is known that, since ATP synthesis and butyrate production pathways in microorganisms require hydrogen ions, carbon dioxide that generates carbonic acid and hydrogen ions when dissolved in water is an essential component of an appropriate mixed gas for the growth of anaerobic microorganisms (Killam et al., J. Clin. Microbiol., 2003, 41:2201-2202; Reilly et al., J. Med. Microbiol., 1980, 13:573-579; Stalons et al., Appl. Microbiol. 1974, 27:1098-1104).

A generally known gas composition for culturing *Faecalibacterium prausnitzii* species is 90% $N_2$+5% $CO_2$+5%

$H_2$, 80% $N_2$+10% $CO_2$+10% $H_2$, 81% $N_2$+11% $CO_2$+8% $H_2$, or 97% $CO_2$+3% $H_2$, which comprises 5% to 97% $CO_2$. However, in mass culture of *Faecalibacterium prausnitzii*, there is a problem in that economic feasibility is low because it is not easy to add $CO_2$. When culturing is performed only in 100% $N_2$ to overcome the problem of low economic feasibility, as can be seen in Korean Patent No. 10-2245415, the lag phase is significantly delayed when a *Faecalibacterium prausnitzii* strain is cultured in an anaerobic gas composed only of 100% $N_2$.

In order to examine whether high-density culture is possible without using the animal-derived component sodium caseinate while overcoming the economic feasibility problem of a mass culture system through culturing in high-purity nitrogen (100% $N_2$) anaerobic gas, the difference in culturability between the presence and absence of a carbonate compound and sodium caseinate was examined by culturing strains of phylogroup II.

As a basal medium, a medium (hereinafter referred to as "SPYE w/MAC") containing the following components on the basis of the results of the above Examples and pretreated with 0.05% w/v L-cysteine was used: 20 g/L soy-peptone, 10 g/L yeast extract, 12.5 g/L maltose, 6 g/L ammonium acetate, and 0.1 mg/L cyanocobalamin ($B_{12}$). As shown in Table 9 below, a phosphate compound ($K_2HPO_4$, $KH_2PO_4$) for buffering action and a carbonate compound ($KHCO_3$) capable of buffering action and generating hydrogen ions and $CO_2$ through the reaction formula $CO_2$+$H_2 \leftrightarrow H_2CO_3 \leftrightarrow HCO_3^- +H^+$ were derived, and culturability in media combined with the carbonate compound ($KHCO_3$) was examined. Since the carbonate compound generates $CO_2$ by thermal decomposition, it was separately added through filtration sterilization rather than sterilization by autoclaving. In addition, as can be seen in Table 10 below, it was confirmed that, among potassium hydrogen carbonate ($KHCO_3$) and sodium hydrogen carbonate ($NaHCO_3$), which are representative carbonate compounds, potassium hydrogen carbonate having a high thermal decomposition temperature and solubility was more suitable for large-scale fermentation.

TABLE 9

| Parameters | Function | Issue | Modification | Advantage |
| --- | --- | --- | --- | --- |
| Medium component | | | | |
| $K_2HPO_4$ | Adjust and control pH | Precipitation and basification | $K_2HPO_4$/ $KH_2PO_4$ + $KHCO_3$ | $CO_2$ production and high buffering capacity |
| Gas type | | | | |
| 80% $N_2$ and 20% $CO_2$ (or 90% $N_2$, 5% $CO_2$, and 5% $H_2$) | Anaerobic condition | High cost and acidification | 100% $N_2$ | Low cost and easy to use |

TABLE 10

| Chemical formula | CAS No. | MW | pH | Water solubility (at 20° C.) | Thermal decomposition temperature | Acidity (pKa) | $LD_{50}$ (rat, oral) |
| --- | --- | --- | --- | --- | --- | --- | --- |
| $NaHCO_3$ | 144-55-8 | 84.007 | 8.5 (1% solution) | 96 g/L | 80 to 100° C. ($CO_2$ production) | 10.329 | 4,220 mg/kg |
| $KHCO_3$ | 298-14-6 | 100.115 | 8.2 (1% solution) | 224 g/L | 100 to 120° C. ($CO_2$ production) | 10.329 | 2,825 mg/kg |

TABLE 11

| Strains | Basal media | Supplements (g/L)[2] | | | | Culture condition (gas type) | Growth ($\Delta OD_{600}$)[*,†] |
| --- | --- | --- | --- | --- | --- | --- | --- |
| | | $K_2HPO_4$ | $KH_2PO_4$ | $KHCO_3$ | NaCAS | | |
| EB-FPDK11 | SPYE w/MAC | 0.45 | 0.45 | 0 | — | 100% $N_2$ | 0.138 ± 0.003 |
| | | 0.45 | 0.45 | 2 | — | | 0.698 ± 0.005 |
| | | 0.45 | 0.45 | 4 | — | | 0.379 ± 0.003 |
| | | 0.45 | 0.45 | 8 | — | | 0.051 ± 0.002 |
| | | 0.45 | 0.45 | 0 | 2.5 | | 0.329 ± 0.015 |
| | | 0.45 | 0.45 | 2 | 2.5 | | 0.988 ± 0.008 |
| | | 0.45 | 0.45 | 4 | 2.5 | | 0.857 ± 0.016 |
| | | 0.45 | 0.45 | 8 | 2.5 | | 0.101 ± 0.006 |
| EB-FPYYK1 | SPYE w/MAC | 0.45 | 0.45 | 0 | — | 100% $N_2$ | 0.051 ± 0.002 |
| | | 0.45 | 0.45 | 2 | — | | 0.541 ± 0.009 |
| | | 0.45 | 0.45 | 4 | — | | 0.648 ± 0.009 |
| | | 0.45 | 0.45 | 4 | 2.5 | | 0.014 ± 0.003 |
| A2-165 | SPYE w/MAC | 0.45 | 0.45 | 0 | — | 100% $N_2$ | 0.064 ± 0.004 |
| | | 0.45 | 0.45 | 2 | — | | 0.610 ± 0.018 |
| | | 0.45 | 0.45 | 4 | — | | 0.871 ± 0.017 |
| | | 0.45 | 0.45 | 4 | 2.5 | | 0.36 0.001 |

As can be seen from Table 11 above and FIG. 16, in the 100% $N_2$ condition, there was a significant difference in culturability between the presence and absence of potassium hydrogen carbonate. The EB-FPDK11 strain showed the highest absorbance at a potassium hydrogen carbonate concentration of 2 g/L, and the cellular morphology was observed to be a very short rod shape. In addition, when the viable cell counts of the strain cultured in the presence or absence and sodium caseinate were calculated, they were $3.2\times10^{11}$ CFUs/mL and $5.3\times10^{11}$ CFUs/mL, respectively, which did not significantly differ. It was confirmed that, in the 100% $N_2$ condition, the EB-FPYYK1 and A2-165 strains showed the highest increase in the absorbance at a potassium hydrogen carbonate concentration of 4 g/L rather than 2 g/L, the viable cell count of the EB-FPYYK1 strain was $3.0\times10^{10}$ CFUs/mL, and the viable cell count of the A2-165 strain was $2.7\times10^{11}$ CFUs/mL. However, it was shown that, when the culture medium for the EB-FPYYK1 strain or the A2-165 strain was combined with sodium caseinate, culturability significantly decreased rather than increased, and thus an aspect somewhat different from the EB-FPDK11 strain appeared.

In conclusion, it was confirmed that culture under $CO_2$-free gas conditions was possible through the combination of the phosphate compound and the carbonate compound, and that high-density culture at about $10^{11}$ CFUs/mL was possible even in the medium composition free of animal-derived components.

The invention claimed is:

1. A medium composition for culturing *Faecalibacterium prausnitzii* phylogroup II, to a density of $10^{10}$ to $10^{11}$ CFUs/mL comprising vegetable peptone, yeast extract, a phosphate compound, a carbonate compound, cyanocobalamin, L-cysteine, ammonium acetate, and maltose, wherein the vegetable peptone is present in an amount of 10-20 g/L, the yeast extract is present in an amount from 5-10 g/L, the phosphate compound is selected from disodium phosphate ($Na_2HPO_4$), dipotassium phosphate ($K_2HPO_4$) or potassium phosphate ($KH_2PO_4$) or mixtures thereof, and is present in an amount to provide a medium composition pH of 6.5 to 8.0, the maltose is present in an amount from 2.5-30 g/L, the carbonate compound is potassium hydrogen carbonate and is present in an amount from 2-6 g/L, and the ammonium acetate is present in an amount from 2-16 g/L.

2. The medium composition of claim 1, wherein the maltose is present at a concentration of 2.5 to 20 g/L.

3. The medium composition of claim 1, wherein the carbonate compound is present at a concentration of 3 to 6 g/L.

4. The medium composition of claim 1, wherein the ammonium acetate is present at a concentration of 2 to 12 g/L.

5. A method for culturing *aecalibacterium prausnitzii* comprising steps of:
a) inoculating *Faecalibacterium prausnitzii* into the medium composition of claim 1; and
b) culturing the inoculated *Faecalibacterium prausnitzii* under conditions of a temperature of 35 to 38° C., a pH of 6.5 to 7, and a gas flow rate of 0.1 to 0.3 L/h, wherein the cultured *Faecalibacterium prausnitzii* phylogroup II has a density of $10^{10}$ to $10^{11}$ CFUs/mL.

* * * * *